(12) United States Patent
Madden et al.

(10) Patent No.: US 8,034,595 B2
(45) Date of Patent: Oct. 11, 2011

(54) NITRILASES AND METHODS FOR MAKING AND USING THEM

(75) Inventors: Mark Madden, La Mesa, CA (US); David Weiner, Del Mar, CA (US); Jennifer Ann Chaplin, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 836 days.

(21) Appl. No.: 11/868,909

(22) Filed: Oct. 8, 2007

(65) Prior Publication Data

US 2009/0162906 A1 Jun. 25, 2009

Related U.S. Application Data

(62) Division of application No. 09/751,299, filed on Dec. 28, 2000, now Pat. No. 7,300,775.

(60) Provisional application No. 60/173,609, filed on Dec. 29, 1999, provisional application No. 60/254,414, filed on Dec. 7, 2000.

(51) Int. Cl.
*C12N 9/14* (2006.01)
*C12P 13/04* (2006.01)
*C07H 21/04* (2006.01)

(52) U.S. Cl. ........ 435/195; 530/350; 435/106; 536/23.2

(58) Field of Classification Search .................. 530/350; 536/23.2; 435/106, 195
See application file for complete search history.

(56) References Cited

U.S. PATENT DOCUMENTS

| | | | |
|---|---|---|---|
| 4,611,067 A | 9/1986 | Volante |
| 4,908,313 A | 3/1990 | Satoh et al. |
| 5,097,045 A | 3/1992 | Butler |
| 5,103,024 A | 4/1992 | Millar |
| 5,124,482 A | 6/1992 | Butler |
| 5,149,837 A | 9/1992 | Butler |
| 5,206,158 A | 4/1993 | Clifford et al. |
| 5,587,303 A | 12/1996 | Wakamoto et al. |
| 5,635,391 A | 6/1997 | Petrie |
| 5,756,306 A | 5/1998 | Yamaguchi et al. |
| 5,872,000 A | 2/1999 | Yu |
| 5,939,553 A | 8/1999 | Reichwein |
| 6,042,824 A | 3/2000 | Khalaf |
| 2003/0044800 A1 | 3/2003 | Connelly |

FOREIGN PATENT DOCUMENTS

| | | |
|---|---|---|
| EP | 0 332 379 | 9/1989 |
| EP | 0332379 | 9/1989 |
| EP | 0 449 648 | 10/1991 |
| EP | 0449648 | 10/1991 |
| EP | 0 502 476 | 9/1992 |
| EP | 0502476 | 9/1992 |
| EP | 0 596 812 | 5/1994 |
| EP | 0596812 | 5/1994 |
| EP | 0 610 048 | 8/1994 |
| EP | 0 610 049 | 8/1994 |
| EP | 0610048 | 8/1994 |
| EP | 0610049 | 8/1994 |
| EP | 0 711 836 | 5/1996 |
| EP | 0711836 | 5/1996 |
| EP | 0 773 297 | 5/1997 |
| EP | 0773297 | 5/1997 |
| EP | 0 780 471 | 6/1997 |
| EP | 0780471 | 6/1997 |
| JP | 61-162195 | 1/1985 |
| JP | 61162195 | 7/1986 |
| JP | 63-500004 | 1/1988 |
| JP | 01-317392 | 12/1989 |
| JP | 01317392 | 12/1989 |
| JP | 04-079894 | 3/1992 |
| JP | 04-099495 | 3/1992 |
| JP | 04079894 | 3/1992 |
| JP | 04099495 | 3/1992 |
| JP | 06-237789 | 8/1994 |
| JP | 06237789 | 8/1994 |
| JP | 08-131188 | 5/1996 |
| JP | 08131188 | 5/1996 |
| JP | 63500004 | 1/1998 |
| WO | 86/07386 | 12/1986 |
| WO | WO-86/07386 | 12/1986 |
| WO | 91/02071 | 2/1991 |
| WO | WO-91/02071 | 2/1991 |
| WO | 91/08287 | 6/1991 |
| WO | 91/08316 | 6/1991 |
| WO | WO-91/08287 | 6/1991 |
| WO | WO-91/08316 | 6/1991 |
| WO | 94/24305 | 10/1994 |
| WO | WO-94/24305 | 10/1994 |
| WO | 97/21805 | 6/1997 |
| WO | WO-97/21805 | 6/1997 |
| WO | 98/13119 | 4/1998 |
| WO | WO-98/13119 | 4/1998 |
| WO | 99/55310 | 11/1999 |
| WO | WO-99/55310 | 11/1999 |
| WO | 00/03685 | 1/2000 |
| WO | WO-00/03685 | 1/2000 |
| WO | 00/58504 | 10/2000 |
| WO | WO-00/58504 | 10/2000 |
| WO | 01/04327 | 1/2001 |

(Continued)

OTHER PUBLICATIONS

Guo et al., Angew Chem. Int. Ed. (1999) 38(12):1755-1758.

(Continued)

*Primary Examiner* — Chih-Min Kam
(74) *Attorney, Agent, or Firm* — Brian W. Siddons; Lynn M. Linkowski

(57) ABSTRACT

The invention provides nitrilases and methods for making and using them, and in one aspect, provides methods for producing enantiomerically pure α-substituted carboxylic acids, such as, for example, α-amino acids and α-hydroxy acids. In one aspect, methods of the invention combine an aldehyde or ketone with a cyanide and ammonia or an ammonium salt or an amine, in the presence of a nitrilase or a polypeptide having nitrilase activity, to stereoselectively hydrolyze the amino nitrile or cyanohydrin intermediate under conditions sufficient to produce the carboxylic acid.

4 Claims, No Drawings

FOREIGN PATENT DOCUMENTS

| | | |
|---|---|---|
| WO | 01/04331 | 1/2001 |
| WO | WO-01/04327 | 1/2001 |
| WO | WO-01/04331 | 1/2001 |
| WO | 01/14561 | 3/2001 |
| WO | 01/18211 | 3/2001 |
| WO | 01/21782 | 3/2001 |
| WO | WO-01/14561 | 3/2001 |
| WO | WO-01/18211 | 3/2001 |
| WO | WO-01/21782 | 3/2001 |
| WO | 01/25438 | 4/2001 |
| WO | 01/29241 | 4/2001 |
| WO | WO-01/25438 | 4/2001 |
| WO | WO-01/29241 | 4/2001 |
| WO | WO01/48175 | 7/2001 |
| WO | 02/29079 | 4/2002 |
| WO | WO-02/29079 | 4/2002 |
| WO | WO02/29079 | 4/2002 |
| WO | 03/00840 | 1/2003 |
| WO | 03/04456 | 1/2003 |
| WO | 03000840 A2 | 1/2003 |
| WO | WO2004/096988 | 11/2004 |

OTHER PUBLICATIONS

Guo et al., PNAS USA (2004) 101:9205-9210.
Hughes et al., "Application of whole cell rhodococcal biocatalysts in acrylic polymer manufacture" Antonie Van Leeuwenhoek (1998) 74, Abstract, Jul.-Oct.
Iyer et al., Amino Acids (1996) 11(304):259-268.
Kim et al., Enzyme and Microbial Tech. (2000) 27:492-501.
Kobayashi et al., Curr. Op. in Chem. Biol. (2000) 4:95-102.
Kobayashi et al., Eur. J. Biochem. (1989) 182:349-356.
Kobayashi et al., FEBS Lett. (1998) 439(3):325-328.
Komeda et al., PNAS USA (1996) 93(20):10572-10577.
Levy-Schil et al., Gene (1995) 161(1):15-20.
Liu et al., Anal. Chem. (1995) 67, Abstract.
Mala et al., Carbo. Rsrch. (1999) 322:209-218.
Martino et al., Proc. Biochem. (1996) 31(3):281-285.
Nagasawa et al.,Tibtech (1989) 7:153-158.
Novo et al., Febs Letts (1995) 367(3):275-279.
Ogawa et al., Trends in Biotech (1999) 17(1):13-20.
Reetz et al., Angew Chem. Int. Ed. (1999) 38(12):1758:1761.
Reetz, Angew Chem. Int. Ed. (2002) 41(8):1335-1338.
Robertson et al., Applied and Environ. Microbiol. (2004) 70(4):2429-2436.
Rouhi, Cenear (2002) 80(23):51-57.
Schrader et al., Can. J. Chem. (2002) 80:626-632.
Shen et al., Israel J. of Chem. (2001) 41:313-316.
Taillades et al., Bulletin De La Societe Chimique De France (1991) 128(3):423-430.
Tao et al., Anal. Chem. (2002) 74:3783-3789.
Wanatabe et al., Applied Microbiol. and Biotech. (1998) 50(1):93-97.
Wiyakrutta et al., J. of Biotech. (1997) 55(3):193-203.
Wu et al., Anal. Letts (1997) 30(7):1399-1406.
Zhao et al., J. of Chromatog. B (1994) 656:441-446.
Zhou et al., "Nucleotide sequence of a pathogen induced nitrilase gene from Arabidopsis thaliana: Nit2 (Accession No. U47114)" Plant Gene Register PGR 96-006 (1995).
EP 08075753.7—Extended European Search Report—Jun. 25, 2009.
PCT/US2008/55569-ISR & WO-Oct. 14, 2008.
EP08731180—Extended European Search Report—Jul. 2, 2010.
EP03753097—Supplementary Partial EP Search Report—Sep. 21, 2007.
EP03753097—EP Office Action—Aug. 11, 2010.
EP10177452—Extended EP Search Report—Nov. 5, 2010.
EPO—Oct. 13, 2010—94(3) Communication—00989578.
Desantis—Journal of the American Chemical Society (2002)-124-9024-9026.
USPTO—Dec. 12, 2007—Office Action—10/514,004.
USPTO—Feb. 3, 2009—Final Office Action—10/514,004.
Robertson—Applied and Environmental Microbiology (2004)-70-2429-2436.
Abato et al., J. Am. Chem. Soc. (2001) 123:9206-9207.
Almatawah et al., Enzyme and Microbial. Tech. (1999) 25:718-724.
Baumann et al., Poster P-130, presented at Bio Trans 2001, Sep. 2-7, 2001, Dramstadt, Germany.
Bhalla et al., App. Micro Biotech (1992) 37:184-190.
Bork et al., Protein Science (1994) 3(8):1344-1346.
Business Communications Company, Amino Acids for Synthesis Applications—Introduction, Summary, Overview, Industry, Manufacture of Amino Acids, Peptide Synthesis Technologies and Amino Acid Products for Synthesis Use Section 7.3 Unnatural Amino Acids, Feb. 1999, 9 pgs.
Business Communications Company, Amino Acids for Synthesis Applications—Introduction, Summary, Overview, Industry, Manufacture of Amino Acids, Peptide Synthesis Technologies and Amino Acid Products for Synthesis Use Section 7.2.5 Prices of Natural Amino Acids, (1999).
Caruso et al., Physicochem. and Engineering Aspects (2000) 169:287-293.
Cheong et al., Enzyme and Microbial Tech. (2000) 26:152-158.
Choi et al., Arch. Pharm. Res. (1986) pp. 45-47.
Cowan et al., Extremophiles (1998) 2:207-216.
Crosby et al., Tetrahedron Asymmetry (1992) 3(12):1547-1550.
Database WPI Section Ch, Week 199217, Derwent Publications Ltd., London, GB; Class B05, AN 1992-137926, XP002165677.
Diaz et al., Tetra Letters (2001) 42:2617-2619.
Dufour et al., FEBS Letters (1998) 433:78-82.
Duran et al., Biosci. Biotech. Biochem. (1993) 57(8):1323-1328.
Fournand et al., J. of Mole. Catalysis B: Enzymatic (1998) 5:207-211.
Gabriel et al., J. of Chromato. B (1996) 681:191-195.
Gallifuoco et al., Process Biochem. (1999) 35:179-185.
GenBank Accession No. E01313, Sep. 29, 1997.
Graham et al., Enzyme and Microbial Tech. (2000) 26:368-373.
Abato—J. Am. Chem. Soc. (2001)-123-9206-9207.
Almatawah—Enzyme and Microbial Technology (1995)-25-718-724.
Baumann—5th BioTrans Conference—Poster P-130 (2001) Dramstadt Univ. of Tech.
Bork—Protein Science (1994)-3-1344-1346.
Choi—Arch. Pharm. Res. (1986)-9-45-47.
Caruso—Colloids and Surfaces A: Psysicochemical and Engineering Aspects (2000)-169-287-293.
Duran—Biosci. Biotech. Biochem. (1993)-57-1323-1328.
Komeda—PNAS USA (1996)-93-10572-10577.
Levy-Schil—Gene (1995)-161-15-20.
Novo—FEBS Letters (1995)-367-275-279.
Watanabe—Applied Microbiology and biotechnology (1998)-50-93-97.
Wiyakrutta—Journal of Biotechnology (1997)-55-193-203.
Business Communications Company, Amino Acids for Synthesis Applications, Section 7.2.5 Prices of Natural Amino Acids—Feb. 1999.
Business Communications Company, Amino Acids for Synthesis Applications—Peptide Synthesis Technologies and Amino Acid Products for Synthesis Use Section 7.3 Unnatural Amino Acids—Feb. 1999.
Iyer—Amino Acids (1996)-11-259-268.
Guo—PNAS (2004)-101-9205-9210.
Bhalla—Applied Micro Biotech (1992)-37-184-190.
Cheong—Enzyme and Microbial Technology (2000)-26-152-158.
Cowan—Extremophiles (1988)-2-207-216.
Crosby—Tetrahedron: Asymmetry (1992)-3-1547-1550.
Dufour—FEBS Letters (1998)-433-78-82.
Gallifuoco—Process Chemistry (1999)-35-179-185.
Genbank Accession No. E01313-(1997)-Deibitsudo.
Graham—Enzyme and Microbial Technology (2000)-26-368-373.
Hughes et al.—International Journal of General and Molecular Microbiology (1998) Application of whole cell rhodococcal biocatalysts in acrylic polymer manufacture, Antoine Van Leeuwenhoek—74—Abstract Only.
Zhao—J. of Chromotog. B. (1994)-656-441-446.
Liu—Anal. Chem. (1995)-67-1679.
Mala—Carbohydrate Research (1999)-322-209-218.
Martino—Process Biochemistry (1996)-128-281-285.
Taillades—Bull. Soc. Chim. Fr. (1991)-128-423-429.

Zhou—Nucleotide Sequence of a Pathogen-Induced Nitrilase Gene from Arabidopsis thaliana: Nit2 (Accession No. U47114) Plant Gene Register (PGR 96-006), (1996) Plant Physiol. 110—p. 1048.
Database WPI Section Ch. Week 199217, Derwent Publications Ltd. London, GB; AN 1992-137926 (1990).
Kobayashi—FEBS Letters (1998)-439-325-328.
Kobayashi—Current Opinion in Chemical Biology (2000)-4-95-102.
Ogawa—Trends in Biotechnology (1999)-17-13-20.
Fournand—Journal of Molecular Catalysis B: Enzymatic (1998)-5-207-211.
Nagasawa—Tibtech (1989)-7-153-158.
Kim—Enzyme and Microbial Technology (2000)-27-492-501.
Gabriel—Journal of Chromatography B. (1996)-681-191-195.
Diaz—Tetra Letters (2001)-42-2617-2619.
Guo—Angew Chem Int Ed (1999)-38-1755-1758.
Reetz—Angew Chem Int. Ed. (1999)-38-1758-1761.
Reetz—Angew Chem Int. Ed. (2002)-41-1335-1338.
Rouhi—Cenear (2002)-80-51-57.
Schrader—Can. J. Chem. (2002)-80-626-632.
Shen—Israel J. of Chem. (2001)-41-313-316.
Tao—Anal. Chem. (1994)-74-3783-3789.
Wu—Anal. Lets (1997)-30-1399-1406.
EPO—Feb. 8, 2008—94(3) Communication—EP00989578.
Branden—Introduction to Protein Structure (1991)-247-268, chpater 16.
Brower—Tetrahedron Letters (1992)-33-2279-2282.
EPO—Apr. 15, 2011—EP Extended Search Report—10190399.5.
Cohen—Tetrahedron Letters (1990)-31-7223-7226.
Gavagan—J. Org. Chem. (1998)-63-4792-4801.
PCT/US2003/15712—International Search Report & Written Opinion—Jan. 5, 2006.
Kobayashi—Eur. J. Biochem. (1989)-182-349-356.
Kobayashi—Tetrahedron (1990)-46-5587-5590.
EP02780877.3—Supplementary EP Search Report—May 8, 2008.
Stalker—J. Biol. Chem. (1988)-263-6310-6314.
Yao—"Discovery of Asymmetric Catalysts Using Kinetic Resolution/Mass Spectrometry Screening" (Abstract) Pap American Chemical Society, 221st ORGN—606 (2001).
Zhao—Plant Physiol. (1996)-110-1047-1048.
EPO—Jan. 12, 2010—94(3) Communication—08075753.7.
USPTO—Feb. 4, 2011—Non Final Office Action—12/773,317.
CIPO—Feb. 1, 2010—Office Action—CA 2486062.
EPO—Apr. 15, 2011—EP Extended Search Report—10189100.0.
EPO—Apr. 11, 2011—EP Search Report—10190401.9.
EPO—Apr. 15, 2011—EP Extended Search Report—10190397.9.

NITRILASES AND METHODS FOR MAKING AND USING THEM

RELATED APPLICATIONS

This application is a divisional patent application claiming priority to U.S. patent applications Ser. No. 09/751,299, filed Dec. 28, 2000, now U.S. Pat. No. 7,300,775; which claims priority under 35 U.S.C. §119(e)(1) to U.S. Provisional applications Ser. No. 60/173,609, filed Dec. 29, 1999 and Ser. No. 60/254,414, filed Dec. 7, 2000. Each of the aforementioned applications are expressly incorporated herein by reference in their entirety and for all purposes.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 564462006610Seqlist.txt | Dec. 4, 2008 | 15,871 bytes |

FIELD OF THE INVENTION

The present invention relates generally to methods for producing enantiomerically pure α-substituted carboxylic acids. The invention provides nitrilases and methods for making and using them, and in one aspect, to methods for producing enantiomerically pure α-amino acids in a single reaction vessel comprising the use of a stereoselective nitrilase in the presence of a cyanide compound, an ammonia or amine compound, and an aldehyde or a ketone.

BACKGROUND OF THE INVENTION

The continuing importance of asymmetric organic synthesis in drug design and discovery has fueled the search for new synthetic methods and chiral precursors. This research effort has resulted in the identification of many new synthetic methods and chiral precursors which have been utilized in developing complex molecules of biological interest.

One important class of chiral molecules are the α-substituted carboxylic acids. These molecules have long been recognized as important chiral precursors to a wide variety of complex biologically active molecules. In particular, a great deal of research effort has been dedicated to the development of methods for the synthesis of enantiomerically pure α-amino acids. Recently, there has been an increasing demand for enantiomerically pure α-amino acids for a variety of uses, including, for example, chiral medicines.

A common synthetic route to α-amino acids is the Strecker synthesis, shown below:

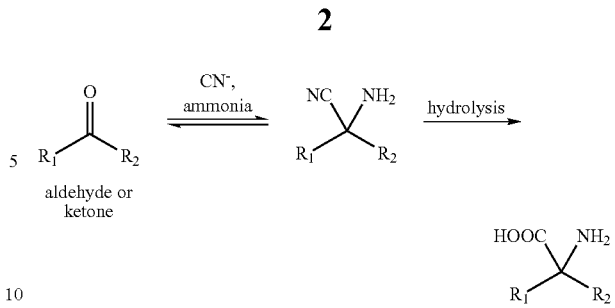

Reversible addition of cyanide and ammonia to the aldehyde or ketone produces an amino nitrile intermediate, which, upon hydrolysis, yields the desired α-amino acid. Although this synthesis has been used to produce racemic amino acids on an industrial scale, there has been only moderate success in developing chiral versions of the Strecker synthesis.

Accordingly, there is a need in the art for efficient, inexpensive, high-yield synthetic methods for producing enantiomerically pure α-substituted carboxylic acids, such as, for example, α-amino acids and α-hydroxy acids.

SUMMARY OF THE INVENTION

In accordance with the present invention there are provided methods for producing enantiomerically pure α-substituted carboxylic acids, such as, for example, α-amino acids and α-hydroxy acids. The methods include combining an aldehyde or ketone with a cyanide and an ammonia-containing compound or an ammonium salt, in the presence of a nitrilase which stereoselectively hydrolyzes the amino nitrile or cyanohydrin intermediate, under conditions sufficient to produce the carboxylic acid.

In a first embodiment, the invention provides a method for producing an enantiomerically pure α-substituted carboxylic acid. The method includes contacting an aldehyde or ketone with a cyanide containing compound and an ammonia-containing compound or an ammonium salt or an amine, and stereoselectively hydrolyzing the resulting amino nitrile or cyanohydrin intermediate with a nitrilase or a polypeptide having nitrilase activity, wherein the nitrilase is sufficiently active to perform the hydrolysis in the presence of the reaction components, under conditions and for a time sufficient to produce the carboxylic acid.

In another aspect of the invention, there are provided compounds produced by the methods set forth herein.

In yet another embodiment, the invention provides nitrilase polypeptides and nucleic acid sequences encoding such nitrilase polypeptides. It should be understood that these nitrilase polypeptides are illustrative of polypeptides useful in the method of the invention, however, the method is not limited to the use of these particular polypeptides. In one aspect, the invention provides a substantially purified polypeptide having an amino acid sequence as set forth in SEQ ID NO:2 or SEQ ID NO:4 and sequences having at least 70% identity thereto and having nitrilase activity.

In another aspect, the invention provides an isolated nucleic acid sequence encoding an amino acid sequence as set forth in SEQ ID NO:2 or SEQ ID NO:4 and sequences having at least 70% identity thereto and having nitrilase activity, and fragments thereof that hybridize to the nucleic acid sequence.

DETAILED DESCRIPTION OF THE INVENTION

In accordance with the present invention, there are provided methods for producing enantiomerically pure α-substituted carboxylic acids. The methods of the invention include contacting an aldehyde or ketone with a cyanide-containing compound, preferably a metal or gaseous cyanide compound, and an ammonia-containing compound or an ammonium salt or an amine, and stereoselectively hydrolyzing the resulting amino nitrile or cyanohydrin intermediate with a nitrilase, wherein the nitrilase is sufficiently active to perform the hydrolysis in the presence of cyanide and ammonia. This stereoselective synthesis is outlined in Scheme 1.

Scheme 1

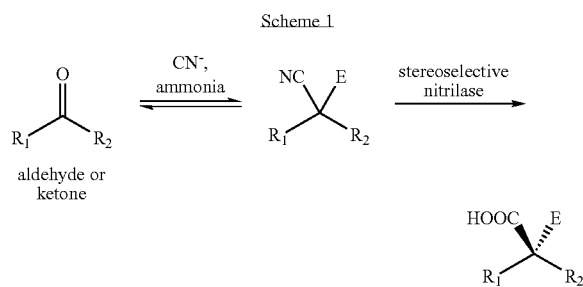

aldehyde or ketone

Since the formation of the amino nitrile or cyanohydrin is a reversible process, the use of a stereoselective nitrilase provides chiral induction, thereby producing the desired amino acid or hydroxy acid enantiomer in 100% theoretical yield. Indeed, even aryl aldehydes and ketones (wherein the equilibrium disfavors amino nitrile or cyanohydrin formation) are effectively converted to chiral α-carboxylic acids. Moreover, since the stereoselective nitrilases contemplated for use in the practice of the present invention are able to perform the hydrolysis in the presence of cyanide and ammonia, invention methods provide the additional advantage of producing the desired enantiomerically pure α-substituted carboxylic acids in a single reaction vessel. In an exemplary model, the nitrilase is SEQ ID NO:2 or SEQ ID NO:4, however, the method is not so limited.

The enantiomerically pure α-substituted carboxylic acids produced by the methods of the present invention have the following structure:

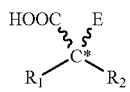

wherein:
R$_1$ and R$_2$ are each independently —H, substituted or unsubstituted alkyl, alkenyl, alkynyl, aryl, heteroaryl, cycloalkyl, heterocyclic, wherein the substituents are lower alkyl, hydroxy, alkoxy, mercapto, cycloalkyl, heterocyclic, aryl, heteroaryl, aryloxy, or halogen or optionally R$_1$ and R$_2$ are linked to cooperate to form a functional cyclic moiety, and
E is —N(R$_x$)$_2$ or —OH, wherein each R$_x$ is —H or lower alkyl.

As used herein, the term "alkyl" refers to a monovalent straight or branched chain or cyclic radical of from one to twenty-four carbon atoms, including methyl, ethyl, n-propyl, isopropyl, n-butyl, isobutyl, tert-butyl, n-hexyl, and the like. The term "lower alkyl" refers to a monovalent straight or branched chain or cyclic radical of from one to about six carbon atoms.

As used herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As used herein, "alkenyl" refers to straight or branched chain hydrocarbyl groups having one or more carbon-carbon double bonds, and having in the range of about 2 up to 24 carbon atoms, and "substituted alkenyl" refers to alkenyl groups further bearing one or more substituents as set forth above.

As used herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynylene groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

In preferred embodiments, the enantiomerically pure α-substituted carboxylic acid produced by the methods of the present invention is an α-amino acid or α-hydroxy acid. In particularly preferred embodiments the enantiomerically pure α-amino acid is D-phenylalanine, D-phenylglycine, L-methylphenylglycine, L-tert-leucine, D-alanine, or D-hydroxynorleucine, R-pantolactone, 2-chloromandelic acid, (S)- and (R)-mandelic acid and the enantiomerically pure α-hydroxy acid is (S)-cyclohexylmandelic acid.

Aldehydes and ketones contemplated for use in the practice of the present invention have the following structure:

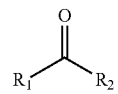

wherein R$_1$ and R$_2$ are as defined above. In preferred embodiments, at least one of R$_1$ and R$_2$ is an aryl group.

Metal cyanides contemplated for use in the practice of the present invention include the alkali metal cyanides LiCN, NaCN, KCN, RbCN, and CsCn. Preferred alkali metal cyanides include LiCN, NaCN, and KCN. A most preferred alkali metal cyanide is KCN. In addition, gaseous cyanides are useful in the method of the invention.

Ammonia or an ammonium salt or an amine may be used in accordance with the present invention. Ammonium salts contemplated for use in the practice of the present invention have the formula NH$_2$(R)$_2$$^+$X$^-$, wherein each R is independently —H or lower alkyl, and X is fluoride, chloride, bromide, or iodide or any counter ion. Thus, when R is lower alkyl, the methods of the present invention also provide N-substituted or N,N-disubstituted enantiomerically pure α-amino acids. In a preferred embodiment, the ammonium salt is $NH_4^+Cl^-$.

Nitrilases contemplated for use in the practice of the present invention include those which are sufficiently robust to stereoselectively hydrolyze the transient amino nitrile or cyanohydrin under Strecker conditions, i.e., in the presence of cyanide and ammonia. Such nitrilases include, for example, those set forth in SEQ ID Nos:2 and 4.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. In one embodiment, a "nucleic acid sequence" of the invention includes, for example, a sequence encoding a polypeptide as set forth in SEQ ID Nos: 2 and 4, and variants thereof. In another embodiment, a "nucleic acid sequence" of the invention includes, for example, a sequence as set forth in SEQ ID Nos: 1 and 3, sequences complementary thereto, fragments of the foregoing sequences and variants thereof.

A "coding sequence" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules. In one embodiment, an "amino acid sequence" or "polypeptide sequence" of the invention includes, for example, a sequence as set forth in SEQ ID Nos: 2 and 4, fragments of the foregoing sequences and variants thereof. In another embodiment, an "amino acid sequence" of the invention includes, for example, a sequence encoded by a polynucleotide having a sequence as set forth in SEQ ID Nos: 1 and 3, sequences complementary thereto, fragments of the foregoing sequences and variants thereof.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl.

Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37 degrees C. are ordinarily used, but may vary in accordance with the supplier's instructions. After digestion the gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acid sequences or polypeptides, refers to two or more sequences that have at least 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a nitrilase polypeptide, resulting in modification of the structure of the polypeptide, without significantly altering its biological activity. For example, amino- or carboxyl-terminal amino acids that are not required for nitrilase biological activity can be removed. Modified polypeptide sequences of the invention can be assayed for nitrilase biological activity by any number of methods, including contacting the modified polypeptide sequence with an nitrilase substrate and determining whether the modified polypeptide decreases the amount of specific substrate in the assay or increases the bioproducts of the enzymatic reaction of a functional nitrilase polypeptide with the substrate.

"Fragments" as used herein are a portion of a naturally occurring or recombinant protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 70, but more typically about 85% or more identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of a nitrilase of the invention. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM and any combination thereof.

In one aspect, a non-stochastic method termed synthetic ligation reassembly (SLR), that is somewhat related to stochastic shuffling, save that the nucleic acid building blocks are not shuffled or concatenated or chimerized randomly, but rather are assembled non-stochastically can be used to create variants.

The SLR method does not depend on the presence of a high level of homology between polynucleotides to be shuffled. The invention can be used to non-stochastically generate libraries (or sets) of progeny molecules comprised of over $10^{100}$ different chimeras. Conceivably, SLR can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. Enzymes and polypeptides for use in the invention can be mutagenized in accordance with the methods described herein.

Thus according to one aspect of the invention, the sequences of a plurality of progenitor nucleic acid templates are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made genes produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect variants of the polynucleotides and polypeptides described herein are obtained by the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., SEQ ID Nos: 1 and 3, and combinations thereof) into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from inter-molecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., a hybrid nitrilase). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by original polynucleotides include, but are not limited to, hydrolases, such as nitrilases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Xanthobacter, Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, methods can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome or immediately adjacent to one another and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anticancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. Once ligated into an appropriate vector, two or more vectors containing different nitrilase) gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:
1) introducing at least a first polynucleotide in operable linkage and a second polynucleotide in operable linkage, the at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBLUESCRIPT™ plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

A preferred type of vector for use in the present invention contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al., 1989).

The DNA sequence in the expression vector is operatively linked to an appropriate expression control sequence(s) (promoter) to direct RNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance in E. coli.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, variant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNaseH.
b) Primers that include unique restriction cleavage sites can be utilized. Multiple sites, a battery of unique sequences, and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalyzing the hydrolysis of a nitrile).

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, prior to or during recombination or reassortment, polynucleotides of the invention or polynucleotides generated by the method described herein can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine, see Sun and Hurley, 1992); an N-acetylated or deacetylated 4'-fluoro-4-aminobiphenyl adduct capable of inhibiting DNA synthesis (see, for example, van de Poll et al., 1992); or a N-acetylated or deacetylated 4-aminobiphenyl adduct capable of inhibiting DNA synthesis (see also, van de Poll et al., 1992, pp. 751-758); trivalent chromium, a trivalent chromium salt, a polycyclic aromatic hydrocarbon ("PAH") DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used —either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In a particular exemplification, it is possible to simultaneously mutagenize two or more contiguous amino acid positions using an oligo that contains contiguous N,N,G/T triplets, i.e. a degenerate (N,N,G/T)n sequence.

In another aspect, the present invention provides for the use of degenerate cassettes having less degeneracy than the N,N,G/T sequence. For example, it may be desirable in some instances to use (e.g. in an oligo) a degenerate triplet sequence comprised of only one N, where the N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in one embodiment, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process (es), including saturation mutagenesis, in an iterative manner. In one exemplification, the iterative use of any mutagenizing process(es) is used in combination with screening.

Thus, in a non-limiting exemplification, polynucleotides and polypeptides of the invention can be derived by saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, mutagenesis can be used to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of SEQ ID Nos: 1 and 3, sequences substantially identical thereto, sequences complementary thereto, or a fragment comprising at least 10, 15, 20, 25, 30, 35, 40, 50, 75, 100, 150, 200, 300, 400, or 500 consecutive bases of one of the sequences of SEQ ID Nos: 1 and 3. The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acid sequences of the invention may be used to prepare one of the polypeptides of SEQ ID Nos: 2 and 4, and sequences substantially identical thereto, or fragments comprising at least 5, 10, 15, 20, 25, 30, 35, 40, 50, 75, 100, or 150 consecutive amino acids of one of the polypeptides of SEQ ID Nos: 2 and 4, and sequences substantially identical thereto.

Accordingly, another aspect of the invention is an isolated nucleic acid sequence which encodes one of the polypeptides of SEQ ID Nos: 2 and 4, sequences substantially identical thereto, or fragments comprising at least 5, 10, 15, 20, 25, 30, 35, 40, 50, 75, 100, or 150 consecutive amino acids of one of the polypeptides of SEQ ID Nos: 2 and 4. The coding sequences of these nucleic acids may be identical to one of the coding sequences of SEQ ID Nos: 1 and 3, or a fragment thereof or may be different coding sequences which encode one of the polypeptides of SEQ ID Nos: 2 and 4, sequences substantially identical thereto, and fragments having at least 5, 10, 15, 20, 25, 30, 35, 40, 50, 75, 100, or 150 consecutive amino acids of one of the polypeptides of SEQ ID Nos: 2 and 4, as a result of the redundancy or degeneracy of the genetic code. The genetic code is well known to those of skill in the art and can be obtained, for example, on page 214 of B. Lewin, Genes VI, Oxford University Press, 1997, the disclosure of which is incorporated herein by reference.

The isolated nucleic acid sequence which encodes one of the polypeptides of SEQ ID Nos: 2 and 4, and sequences substantially identical thereto, may include, but is not limited to: only a coding sequence of one of SEQ ID Nos: 1 and 3, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

Alternatively, the nucleic acid sequences of the invention may be mutagenized using conventional techniques, such as site directed mutagenesis, or other techniques familiar to those skilled in the art, to introduce silent changes into the polynucleotides of SEQ ID NOs: 1 and 3, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of the invention (e.g., SEQ ID Nos:2 and 4). Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acid sequences which specifically hybridize to probes comprising at least 10, 15, 20, 25, 30, 35, 40, 50, 75, 100, 150, 200, 300, 400, or 500 consecutive bases of one of the sequences of SEQ ID Nos: 1 and 3, and sequences substantially identical thereto (or the sequences complementary thereto) under conditions of high, moderate, or low stringency as provided herein.

The isolated nucleic acids of SEQ ID Nos: 1 and 3, sequences substantially identical thereto, complementary sequences, or a fragment comprising at least 10, 15, 20, 25, 30, 35, 40, 50, 75, 100, 150, 200, 300, 400, or 500 consecutive bases of one of the foregoing sequences may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", PCR Methods and Applications 1:5-16, 1991; E. Fahy et al., "Self-sustained Sequence Replication (3SR): An Isothermal Transcription-based Amplification System Alternative to PCR", PCR Methods and Applications 1:25-33, 1991; and Walker G. T. et al., "Strand Displacement Amplification-an Isothermal in vitro DNA Amplification Technique", Nucleic Acid Research 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of a sequence as set forth in SEQ ID Nos: 1 and 3, and sequences substantially identical thereto, may also be used in chromosome walking procedures to identify clones containing genomic sequences located adjacent to the nucleic acid sequences as set forth above. Such methods allow the isolation of genes which encode additional proteins from the host organism.

An isolated nucleic acid sequence as set forth in SEQ ID Nos: 1 and 3, sequences substantially identical thereto, sequences complementary thereto, or a fragment comprising at least 10, 15, 20, 25, 30, 35, 40, 50, 75, 100, 150, 200, 300, 400, or 500 consecutive bases of one of the foregoing sequences may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na2EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following formulas:

For probes between 14 and 70 nucleotides in length the melting temperature (Tm) is calculated using the formula: Tm=81.5+16.6(log [Na+])+0.41 (fraction G+C)−(600/N) where N is the length of the probe.

If the hybridization is carried out in a solution containing formamide, the melting temperature may be calculated using the equation: Tm=81.5+16.6(log [Na+])+0.41(fraction G+C)−(0.63% formamide)−(600/N) where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, or at least 70% homology to a nucleic acid sequence as set forth in SEQ ID Nos: 1 and 3, sequences substantially identical thereto, or fragments comprising at least about 10, 15, 20, 25, 30, 35, 40, 50, 75, 100, 150, 200, 300, 400, or 500 consecutive bases thereof, and the sequences complementary to any of the foregoing sequences. Homology may be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to a nucleic acid sequence as set forth in SEQ ID Nos: 1 and 3, or sequences complementary thereto.

Additionally, the above procedures may be used to isolate nucleic acids which encode polypeptides having at least about 99%, at least 95%, at least 90%, at least 85%, at least 80%, or at least 70% homology to a polypeptide having a sequence as set forth in SEQ ID NOs: 2 and 4, sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising a sequence as set forth in SEQ ID Nos: 2 and 4, sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Fungal promoters include the factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene.

After the expression libraries have been generated one can include the additional step of "biopanning" such libraries prior to screening by cell sorting. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) optionally transforming a host with isolated target DNA to produce a library of clones which are screened for the specified biological activity.

The probe DNA used for selectively isolating the target DNA of interest from the DNA derived from at least one microorganism can be a full-length coding region sequence or a partial coding region sequence of DNA for an enzyme of known activity. The original DNA library can be preferably probed using mixtures of probes comprising at least a portion of the DNA sequence encoding an enzyme having the specified enzyme activity. These probes or probe libraries are preferably single-stranded and the microbial DNA which is probed has preferably been converted into single-stranded form. The probes that are particularly suitable are those derived from DNA encoding enzymes having an activity similar or identical to the specified enzyme activity which is to be screened.

The probe DNA should be at least about 10 bases and preferably at least 15 bases. In one embodiment, the entire coding region may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Hybridization techniques for probing a microbial DNA library to isolate target DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Further, it is optional but desirable to perform an amplification of the target DNA that has been isolated. In this embodiment the target DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then screened for clones which display activity for the enzyme of interest.

Having prepared a multiplicity of clones from DNA selectively isolated from an organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened utilizing a FACS machine for such enzyme activity or for a more specific activity. Alternatively, encapsulation techniques such as gel microdroplets, may be employed to localize multiple clones in one location to be screened on a FACS machine for positive expressing clones within the group of clones which can then be broken out into individual clones to be screened again on a FACS machine to identify positive individual clones. Thus, for example, if a clone mixture has hydrolase activity, then the individual clones may be recovered and screened utilizing a FACS machine to determine which of such clones has hydrolase activity. As used herein, "small insert library" means a gene library containing clones with random small size nucleic acid inserts of up to approximately 5000 base pairs. As used herein, "large insert library" means a gene library containing clones with random large size nucleic acid inserts of approximately 5000 up to several hundred thousand base pairs or greater.

As described with respect to one of the above aspects, the invention provides a process for enzyme activity screening of clones containing selected DNA derived from a microorganism which process includes: screening a library for specified enzyme activity, the library including a plurality of clones, the clones having been prepared by recovering from genomic DNA of a microorganism selected DNA, which DNA is selected by hybridization to at least one DNA sequence which is all or a portion of a DNA sequence encoding an enzyme having the specified activity; and transforming a host with the selected DNA to produce clones which are screened for the specified enzyme activity.

In one embodiment, a DNA library derived from a microorganism is subjected to a selection procedure to select therefrom DNA which hybridizes to one or more probe DNA sequences which is all or a portion of a DNA sequence encoding an enzyme having the specified enzyme activity by:
  (a) rendering the double-stranded genomic DNA population into a single-stranded DNA population;
  (b) contacting the single-stranded DNA population of (a) with the DNA probe bound to a ligand under conditions permissive of hybridization so as to produce a double-stranded complex of probe and members of the genomic DNA population which hybridize thereto;
  (c) contacting the double-stranded complex of (b) with a solid phase specific binding partner for said ligand so as to produce a solid phase complex;
  (d) separating the solid phase complex from the single-stranded DNA population of (b);
  (e) releasing from the probe the members of the genomic population which had bound to the solid phase bound probe;
  (f) forming double-stranded DNA from the members of the genomic population of (e);
  (g) introducing the double-stranded DNA of (f) into a suitable host to form a library containing a plurality of clones containing the selected DNA; and
  (h) screening the library for the specified enzyme activity.

In another aspect, the process includes a preselection to recover DNA including signal or secretion sequences. In this manner it is possible to select from the genomic DNA population by hybridization as hereinabove described only DNA which includes a signal or secretion sequence. The following paragraphs describe the protocol for this embodiment of the invention, the nature and function of secretion signal sequences in general and a specific exemplary application of such sequences to an assay or selection process.

A particularly embodiment of this aspect further comprises, after (a) but before (b) above, the steps of:
  (ai) contacting the single-stranded DNA population of (a) with a ligand-bound oligonucleotide probe that is complementary to a secretion signal sequence unique to a given class of proteins under conditions permissive of hybridization to form a double-stranded complex;
  (aii) contacting the double-stranded complex of (ai) with a solid phase specific binding partner for said ligand so as to produce a solid phase complex;
  (aiii) separating the solid phase complex from the single-stranded DNA population of (a);
  (aiv) releasing the members of the genomic population which had bound to said solid phase bound probe; and
  (av) separating the solid phase bound probe from the members of the genomic population which had bound thereto.

The DNA which has been selected and isolated to include a signal sequence is then subjected to the selection procedure hereinabove described to select and isolate therefrom DNA which binds to one or more probe DNA sequences derived from DNA encoding an enzyme(s) having the specified enzyme activity. This procedure is described and exemplified in U.S. Pat. No. 6,054,267, incorporated herein by reference.

In vivo biopanning may be performed utilizing a FACS-based machine. Complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

In some embodiments, the nucleic acid encoding one of the polypeptides of SEQ ID Nos: 2 and 4, sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of SEQ ID Nos: 2 and 4, sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEMI (Promega Biotec, Madison, Wis., USA) pQE70, pQE60, pQE-9 (Qiagen), pD10, psiX174 pBLUE-SCRIPT II KS™, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of SEQ ID Nos: 2 and 4, sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID Nos: 2 and 4, sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of SEQ ID Nos: 2 and 4, sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of SEQ ID NOs: 2 and 4, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11-15, 1989) and Caldwell, R. C. & Joyce G. F., PCR Methods Applic., 2:28-33, 1992, the disclosure of which is incorporated herein by reference in its entirety. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in pending U.S. patent application Ser. No. 08/677,112 filed Jul. 9, 1996, entitled, Method of "DNA Shuffling with Polynucleotides Produced by Blocking or interrupting a Synthesis or Amplification Process", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747-10751, 1994, the disclosure of which is incorporated herein by reference. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10 to 30 ng/ul in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100 μl of reaction mixture is added and PCR is performed using the following regime: 94° C. for 60 seconds, 94° C. for 30 seconds, 50 to 55° C. for 30 seconds, 72° C. for 30 seconds (30 to 45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an E. coli strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548-1552, 1993, the disclosure of which incorporated herein by reference in its entirety. Random and site-directed mutagenesis are described in Arnold, F. H., Current Opinion in Biotechnology, 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in pending U.S. patent application Ser. No. 08/677,112 filed Jul. 9, 1996, entitled, "Method of DNA Shuffling with Polynucleotides Produced by Blocking or interrupting a Synthesis or Amplification Process", and pending U.S. patent application Ser. No. 08/651,568 filed May 22, 1996, entitled, "Combinatorial Enzyme Development".

The variants of the polypeptides of SEQ ID Nos: 2 and 4 may be variants in which one or more of the amino acid residues of the polypeptides of SEQ ID Nos: 2 and 4 are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Other variants are those in which one or more of the amino acid residues of the polypeptides of SEQ ID Nos: 2 and 4 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID Nos: 2 and 4, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 70%, at least about 80%, at least about 85%, at least about 90%, at least about 95%, or more than about 95% homology to one of the polypeptides of SEQ ID Nos: 2 and 4, sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID Nos: 2 and 4, sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID Nos: 2 and 4, sequences substantially identical thereto, or a fragment comprising at least about 5, 10, 15, 20, 25, 30, 35, 40, 50, 75, 100, or 150 consecutive amino acids thereof using any of the programs described herein.

Another aspect of the invention is an assay for identifying fragments or variants of SEQ ID Nos: 2 and 4, or sequences substantially identical thereto, which retain the enzymatic function of the polypeptides of SEQ ID Nos: 2 and 4, and sequences substantially identical thereto. For example the fragments or variants of the polypeptides, may be used to catalyze biochemical reactions, which indicate that said fragment or variant retains the enzymatic activity of the polypeptides in SEQ ID Nos: 2 and 4.

The assay for determining if fragments of variants retain the enzymatic activity of the polypeptides of SEQ ID Nos: 2 and 4, and sequences substantially identical thereto includes the steps of; contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of SEQ ID Nos: 2 and 4, sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing a polypeptide of SEQ ID Nos: 2 and 4, and sequences substantially identical thereto or polynucleotides encoding such polypeptides for hydrolyzing nitriles. In such procedures, a substance containing a nitrile is contacted with one of the polypeptides of SEQ ID Nos: 2 and 4, and sequences substantially identical thereto under conditions which facilitate the hydrolysis of the compound.

The polypeptides of SEQ ID Nos: 2 and 4, sequences substantially identical thereto or fragments comprising at least 5, 10, 15, 20, 25, 30, 35, 40, 50, 75, 100, or 150 consecutive amino acids thereof, may also be used to generate antibodies which bind specifically to the enzyme polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of a polypeptide of SEQ ID Nos: 2 and 4, sequences substantially identical thereto, or fragments of the foregoing sequences.

In immunoaffinity procedures, the antibody is attached to a solid support, such as a bead or other column matrix. The protein preparation is placed in contact with the antibody under conditions in which the antibody specifically binds to one of the polypeptides of SEQ ID Nos: 2 and 4, sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of SEQ ID Nos: 2 and 4, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of, for example, SEQ ID Nos: 2 and 4, or fragments thereof. Alternatively, transgenic mice may be used to express humanized antibodies to these polypeptides or fragments.

Antibodies generated against a polypeptide of SEQ ID Nos: 2 and 4, sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", Methods in Enzymology, Vol 160, pp. 87-116, which is hereby incorporated by reference in its entirety.

As used herein the term "nucleic acid sequence as set forth in SEQ ID Nos: 1 and 3" encompasses a nucleic acid sequence as set forth in SEQ ID Nos: 1 and 3, a sequence substantially identical to one of the foregoing sequences, fragments of any one or more of the foregoing sequences, nucleotide sequences homologous to SEQ ID Nos: 1 and 3 or homologous to fragments of SEQ ID Nos: 1 and 3, and sequences complementary to all of the preceding sequences. The fragments include portions of SEQ ID Nos: 1 and 3 comprising at least 10, 15, 20, 25, 30, 35, 40, 50, 75, 100, 150, 200, 300, 400, or 500 consecutive nucleotides of SEQ ID Nos: 1 and 3, and sequences substantially identical thereto. Homologous sequences and fragments of SEQ ID Nos: 1 and 3, and sequences substantially identical thereto, refer to a sequence having at least 99%, 98%, 97%, 96%, 95%, 90%, 85%, 80%, 75% or 70% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in SEQ ID Nos: 1 and 3. The homologous sequences may be obtained using any of the procedures described herein or may result from the correction of a sequencing error. It will be appreciated that the nucleic acid sequences of the invention can be represented in the traditional single character format (See the inside back cover of Stryer, Lubert. Biochemistry, 3rd edition. W. H Freeman & Co., New York.) or in any other format which records the identity of the nucleotides in a sequence.

As used herein the term "a polypeptide sequence as set forth in SEQ ID Nos: 2 and 4" encompasses s polypeptide sequence as set forth in SEQ ID Nos: 2 and 4, sequences substantially identical thereto, which are encoded by a sequence as set forth in SEQ ID Nos: 1 and 3, polypeptide sequences homologous to the polypeptides of SEQ ID Nos: 2 and 4, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75% or 70% homology to one of the polypeptide sequences of the invention. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of SEQ ID Nos: 2 and 4, and sequences substantially identical thereto. It will be appreciated that the polypeptides of the invention can be represented in the traditional single character format or three letter format (See the inside back cover of Starrier, Lubert. Biochemistry, 3rd edition. W. H Freeman & Co., New York.) or in any other format which relates the identity of the polypeptides in a sequence.

It will be appreciated by those skilled in the art that a nucleic acid sequence and a polypeptide sequence of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in SEQ ID Nos: 1 and 3, and sequences substantially identical thereto, one or more of the polypeptide sequences as set forth in SEQ ID Nos: 2 and 4, and sequences substantially identical thereto. Another aspect of the invention is a computer readable medium having recorded thereon at least 2, 5, 10, 15, or 20 nucleic acid sequences as set forth in SEQ ID Nos: 1 and 3, and sequences substantially identical thereto.

Another aspect of the invention is a computer readable medium having recorded thereon one or more of the nucleic acid sequences as set forth in SEQ ID Nos: 1 and 3, and sequences substantially identical thereto. Another aspect of the invention is a computer readable medium having recorded thereon one or more of the polypeptide sequences as set forth in SEQ ID Nos: 2 and 4, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the invention include systems (e.g., internet based systems), particularly computer systems which store and manipulate the sequence information described herein. One example of a computer system 100 is illustrated in block diagram form. As used herein, "a computer system" refers to the hardware components, software components, and data storage components used to analyze a nucleotide sequence of a nucleic acid sequence as set forth in SEQ ID Nos: 1 and 3, and sequences substantially identical thereto, or a polypeptide sequence as set forth in SEQ ID Nos: 2 and 4. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, a data storage device having retrievably stored thereon reference nucleotide sequences or polypeptide sequences to be compared to a nucleic acid sequence or a polypeptide sequence of the invention, and a sequence comparer for conducting the comparison. The sequence comparer may indicate a homology level between the sequences compared or identify structural motifs in the above described nucleic acid code of SEQ ID Nos: 1 and 3, and sequences substantially identical thereto, or a polypeptide sequence as set forth in SEQ ID Nos: 2 and 4, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in SEQ ID Nos: 1 and 3, and sequences substantially identical thereto, or the polypeptide sequences as set forth in SEQ ID Nos: 2 and 4, and sequences substantially identical thereto.

Another aspect of the invention is a method for determining the level of homology between a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in SEQ ID Nos: 1 and 3 or the polypeptide sequences as set forth in SEQ ID Nos: 2 and 4 through use of the computer program and determining homology between the nucleic acid codes or polypeptide codes and reference nucleotide sequences or polypeptide sequences.

The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of SEQ ID Nos: 1 and 3, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in SEQ ID Nos: 1 and 3, and sequences substantially identical thereto. In one embodiment, the computer program may be a program which determines whether a nucleic acid sequence as set forth in SEQ ID Nos: 1 and 3, and sequences substantially identical thereto, contains a single nucleotide polymorphism (SNP) with respect to a reference nucleotide sequence.

Accordingly, another aspect of the invention is a method for determining whether a nucleic acid sequence as set forth in SEQ ID Nos: 1 and 3, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in SEQ ID Nos: 1 and 3, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in SEQ ID Nos: 1 and 3 or a polypeptide sequence as set forth in SEQ ID Nos: 2 and 4, and sequences substantially identical thereto.

An "identifier" refers to one or more programs which identifies certain features within a nucleic acid sequence or a polypeptide sequence of the invention. In one embodiment, the identifier may comprise a program which identifies an open reading frame in a nucleic acid sequence as set forth in SEQ ID Nos: 1 and 3, and sequences substantially identical thereto.

The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, comprising reading a nucleic acid sequence or a polypeptide sequence through the use of a computer program which identifies features therein and identifying features within the nucleic acid sequence or polypeptide sequence with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in SEQ ID Nos: 1 and 3, and sequences substantially identical thereto, or the polypeptide sequences as set forth in SEQ ID Nos: 2 and 4, and sequences substantially identical thereto, through the use of the computer program and identifying features within the nucleic acid codes or polypeptide codes with the computer program.

In addition, a nucleic acid sequence or a polypeptide sequence of the invention may be stored and manipulated in a variety of data processor programs in a variety of formats. For example, a nucleic acid sequence as set forth in SEQ ID Nos: 1 and 3, and sequences substantially identical thereto, or a polypeptide sequence as set forth in SEQ ID Nos: 2 and 4, and sequences substantially identical thereto, may be stored as text in a word processing file, such as Microsoft WORD™ or WORDPERFECT™ or as an ASCII file in a variety of database programs familiar to those of skill in the art, such as DB2, SYBASE™, or ORACLE™. In addition, many computer programs and databases may be used as sequence comparison algorithms, identifiers, or sources of reference nucleotide sequences or polypeptide sequences to be compared to a nucleic acid sequence as set forth in SEQ ID Nos: 1 and 3, and sequences substantially identical thereto, or a polypeptide sequence as set forth in SEQ ID Nos: 2 and 4, and sequences substantially identical thereto. The following list is intended not to limit the invention but to provide guidance to programs and databases which are useful with the nucleic acid sequences or the polypeptide sequences of the invention.

The programs and databases which may be used include, but are not limited to: MACPATTERN™ (EMBL), DISCOVERYBASE™ (Molecular Applications Group), GENEMINE™ (Molecular Applications Group), LOOK™ (Molecular Applications Group), MACLOOK™ (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), CATALYST™ (Molecular Simulations Inc.), CATALYST/SHAPE™ (Molecular Simulations Inc.), CERIUS$^2$.DBACCESS™ (Molecular Simulations Inc.), HypoGen (Molecular Simulations Inc.), INSIGHT II™, (Molecular Simulations Inc.), DISCOVER™ (Molecular Simulations Inc.), CHARMm™ (Molecular Simulations Inc.), FELIX™ (Molecular Simulations Inc.), DELPHI™, (Molecular Simulations Inc.), QUANTEMM™, (Molecular Simulations Inc.), HOMOLOGY™ (Molecular Simulations Inc.), MODELER™ (Molecular Simulations Inc.), ISIS™ (Molecular Simulations Inc.), QUANTA™/PROTEIN DESIGN™ (Molecular Simulations Inc.), WEBLAB™ (Molecular Simulations Inc.), WEBLAB DIVERSITY EXPLORER™ (Molecular Simulations Inc.), GENE EXPLORER™ (Molecular Simulations Inc.), SEQFOLD™ (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

All of the references mentioned above are hereby incorporated by reference in their entirety. Each of these techniques is described in detail in the references mentioned. DNA can be mutagenized, or "evolved", utilizing any one or more of these techniques, and rescreened to identify more desirable clones.

The invention will now be illustrated by the following working examples, which are in no way a limitation of the present invention.

The invention will now be described in greater detail by reference to the following non-limiting examples.

EXAMPLES

Example 1

Phenylglycinonitrile was prepared using the Strecker reaction conditions as follows:
1 g 98% KCN in 4 ml $H_2O$ in round bottomed flask
1.18 g $NH_4Cl$
Mix at room temp until $NH_4Cl$ has dissolved
Add 2.12 g benzaldehyde in 4 ml methanol
Stir for 2 h using a magnetic stirrer The presence of the product, phenylglycinonitrile was detected by HPLC (7% isocratic MeOH in water; column: Supelcosil LC-18; 5 cm×4.6 mm; 5 μm). After 2 hours, 70% conversion to product was obtained.

Various dilutions of the reaction mixture were made in 0.1 M sodium phosphate buffer (pH 7), ranging from no dilution to a fifty times dilution. Enzyme solutions were prepared by addition of buffer to lyophilized cell lysate preparations. These cell lysates contained nitrilase which had been overexpressed in a *Pseudomonas* host. Two enzyme preparations, SEQ ID NO:2 and SEQ ID NO:4, with final protein concentrations of 10.72 and 15.56 mg/ml of solution, were used. The enzyme solutions (20 μl) were added individually to each of the phenylglycine-containing dilutions (final volume 300 μl). The samples were incubated at room temperature. After 18 hours, the reactions were sampled and run on TLC (4:1:5 1-butanol: acetic acid:water). Phenylglycine was detected in the 10, 25 and 50 times dilutions, with a faint peak appearing in the 5 times dilution, for both enzymes. After 5 days, the reactions were sampled again and analyzed by HPLC. Nitrilase SEQ ID NO:4 showed approximately 10% conversion to product in the 5 times dilution of substrate nitrilase SEQ ID NO:2 converted <5% of the substrate. Higher conversions were obtained for the lower dilutions of Strecker reaction mixture (up to 35% conversion in the 50 times dilution).

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. An isolated, synthetic or recombinant polypeptide having a hydrolase activity and comprising an amino acid sequence:
   (a) encoded by a nucleic acid having the sequence comprising SEQ ID NO: 1;
   (b) encoded by a nucleic acid comprising a sequence having at least 95%, 97% or 99% or complete sequence identity to SEQ ID NO: 1;
   (c) of the peptide as set forth in SEQ ID NO:2;
   (d) having at least 95%, 97% or 99% or complete sequence identity to SEQ ID NO:2;
   (e) of the polypeptide of any of (a) to (d) having a nitrilase activity;
   (f) of the polypeptide of (e) having a nitrilase activity comprising the ability to produce an enantiomerically pure α-substituted carboxylic acid, α-amino acid or α-hydroxy acid;
   (g) of the polypeptide of (e) having a nitrilase activity comprising the ability to stereoselectively hydrolyze a transient amino nitrile or cyanohydrin under Strecker conditions (in the presence of cyanide and ammonia);
   (h) comprising an enzymatically active fragment of the polypeptide of any of (a) to (g);
   (i) of the polypeptide of any of (a) to (h) further comprising an additional amino acid sequence; or
   (j) of the polypeptide of (i), wherein the additional amino acid sequence comprises or consists of a secretory sequence; a proprotein sequence; or, a sequence which facilitates purification, enrichment, or stabilization of the polypeptide.

2. The isolated, synthetic or recombinant polypeptide of claim 1 comprising:
   (a) at least one conservative amino acid substitution;
   (b) the polypeptide of (a), wherein a conservative amino acid substitution comprises:
   replacement of an aliphatic amino acid with another aliphatic amino acid, or replacement of an acidic residue with another acidic residue, or replacement of a residue bearing an amide group with another residue bearing an amide group, or exchange of a basic residue with another basic residue, or replacement of an aromatic residue with another aromatic residue; or
   (c) the polypeptide of (b), wherein a conservative amino acid substitution comprises:
   replacement of an alanine, valine, leucine or isoleucine with an alanine, valine, leucine or isoleucine; replacement of a serine with a threonine or vice versa; replacement of an aspartic acid or glutamic acid with another acidic residue; replacement of an asparagine or glutamine with another residue bearing an amide group; exchange of a lysine or arginine with another basic residue; or replacement of a phenylalanine or tyrosine with another aromatic residue.

3. The isolated, synthetic or recombinant polypeptide of claim 1, further comprising, or contained in, a protein preparation, an extract or a biological sample.

4. The isolated, synthetic or recombinant polypeptide of claim 1, wherein the hydrolase activity comprises the ability to produce an alpha-substituted carboxylic acid by a method comprising:
   (A) (a) providing an aldehyde or a ketone;
   (b) providing a cyanide-containing compound;
   (c) providing an ammonia-containing compound or a compound comprising an ammonium salt or an amine;
   (d) providing a composition comprising a nitrilase, wherein the nitrilase has the amino acid sequence of the polypeptide of claim 1;
   (e) contacting the aldehyde or ketone of step (a) with a cyanide-containing compound step (b) and an ammonia-containing compound or a compound comprising an ammonium salt or an amine of step (e) such that an amino nitrile or a cyanohydrin intermediate is produced; and
   (f) contacting the amino nitrile or cyanohydrin intermediate of step (e) with the composition of step (d) such that the nitrilase hydrolyzes the amino nitrile or cyanohydrin intermediate to produce an alpha-substituted carboxylic acid,
   wherein the α-substituted carboxylic acid has the following structure:

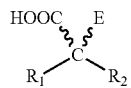

wherein:
$R_1$ and $R_2$ are each independently —H, substituted or unsubstituted alkyl, alkenyl, alkynyl, aryl, heteroaryl, cycloalkyl, heterocyclic, wherein the substituents are lower alkyl, hydroxyl, alkoxy, mercapto, cycloalkyl, heterocyclic, aryl, heteroaryl, aryloxy, or halogen or optionally $R_1$ and $R_2$ are linked to cooperate to form a functional cyclic moiety, and E is —$N(R_x)_2$ or —OH, wherein each $R_x$ is each independently —H or a lower alkyl;

(B) the method of (A), wherein the hydrolase activity comprises the ability to stereoselectively produce an enantiomerically pure α-substituted carboxylic acid having the following structure:

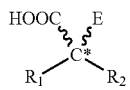

wherein:

$R_1$ and $R_2$ are each independently —H, substituted or unsubstituted alkyl, alkenyl, alkylnyl, aryl, heteroaryl, cycloalkyl, heterocyclic, wherein the substituents are lower alkyl, hydroxyl, alkoxy, mercapto, cycloalkyl, heterocyclic, aryl, heteroaryl, aryioxy, or halogen or optionally $R_1$ and $R_2$ are linked to cooperate to form a functional cyclic moiety, and E is —$N(R_x)_2$ or —OH, wherein each $R_x$ is —H or lower alkyl;

(C) the method of (B), wherein the enantiomerically pure α-substituted carboxylic acid is an α-amino acid;

(D) the method of any of (A) to (C), wherein at least one of $R_1$ and $R_2$ is a substituted or unsubstituted aryl;

(E) the method of (C) or (D), wherein the enantiomerically pure α-amino acid is D-phenylalanine, D-phenylglycine, or L-methylphenylglycine;

(F) the method of (C) or (D), wherein the enantiomerically pure α-amino acid bears a substituted or unsubstituted alkyl side chain;

(G) the method of any of (C) to (F), wherein the enantiomerically pure α-amino acid is L-tert-leucine, D-alanine, or D-hydroxynorleucine;

(H) the method of any of (A) to (D), wherein the enantiomerically pure α-substituted carboxylic acid is an α-hydroxy acid;

(I) the method of any of (A) to (D), wherein the enantiomerically pure α-hydroxy acid is (S)-cyclohexymandelic acid, mandelic acid or 2-chloro mandelic acid;

(J) the method of any of (A) to (I), wherein the cyanide is a metal cyanide or a gaseous cyanide, or the cyanide is an alkali cyanide, or the metal cyanide is sodium cyanide;

(K) the method of any of (A) to (J), wherein the ammonium salt has the formula $NH_2(R)_2^+X$, wherein each R is independently —H or lower alkyl, and X is a counter ion; or (L) the method of (K), wherein X is a halide and/or the halide is $Cl^{31}$, or the ammonium salt is $NH_4^{30}Cl^{31}$.

* * * * *

UNITED STATES PATENT AND TRADEMARK OFFICE
CERTIFICATE OF CORRECTION

PATENT NO.         : 8,034,595 B2                        Page 1 of 1
APPLICATION NO.    : 11/868909
DATED              : October 11, 2011
INVENTOR(S)        : Mark Madden et al.

It is certified that error appears in the above-identified patent and that said Letters Patent is hereby corrected as shown below:

In Column 60
Line 26 in Claim 4, replace "$Cl^{31}$" with "$Cl^-$"

Line 26 in Claim 4, replace "$NH_4^{30}\ Cl^{31}$" with "$NH4^+Cl^-$"

Signed and Sealed this
Twenty-fourth Day of January, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 1041
<212> TYPE: DNA
<213> ORGANISM: Unknown
<220> FEATURE:
<223> OTHER INFORMATION: Description of Unknown Organism: Obtained from
      an environmental sample
<220> FEATURE:
<221> NAME/KEY: CDS
<222> LOCATION: (1)..(1041)

<400> SEQUENCE: 1
```

```
atg tcg gag ccc atg acg aag tat cgc ggc gcg gcg gtg cag gcc gcg         48
Met Ser Glu Pro Met Thr Lys Tyr Arg Gly Ala Ala Val Gln Ala Ala
1               5                   10                  15 ccg gtg ttc ctc gat ctc gac cgc aca gtc gag aaa gcg atc ggc ctg         96
Pro Val Phe Leu Asp Leu Asp Arg Thr Val Glu Lys Ala Ile Gly Leu
                20                  25                  30 atc gag cag gcg gcc aag cag gac gtg cgc ctg atc gca ttc cca gag        144
Ile Glu Gln Ala Ala Lys Gln Asp Val Arg Leu Ile Ala Phe Pro Glu
        35                  40                  45 act tgg att ccc ggc tat ccc ttt tgg ata tgg ctg ggc gcg ccg gct        192
Thr Trp Ile Pro Gly Tyr Pro Phe Trp Ile Trp Leu Gly Ala Pro Ala
    50                  55                  60 tgg ggc atg cgc ttc gtc cag cgc tat ttc gag aat tcg ctc gtg cgc        240
Trp Gly Met Arg Phe Val Gln Arg Tyr Phe Glu Asn Ser Leu Val Arg
65              70                  75                  80 ggc agc aag cag tgg cag gcc ctg gcg gat gcg gcc cgc cgc cac ggc        288
Gly Ser Lys Gln Trp Gln Ala Leu Ala Asp Ala Ala Arg Arg His Gly
                85                  90                  95 atg cat gtc gtg gcc ggc tat agc gag cgc gcg ggc ggc agc ctc tat        336
Met His Val Val Ala Gly Tyr Ser Glu Arg Ala Gly Gly Ser Leu Tyr
            100                 105                 110 atg ggc cag gcg atc ttc ggc ccc gat ggc gat ctg atc gcc gcg cgc        384
Met Gly Gln Ala Ile Phe Gly Pro Asp Gly Asp Leu Ile Ala Ala Arg
        115                 120                 125 cgc aag ctc aag cct acc cat gcg gag cgc acc gtg ttc ggc gag gga        432
Arg Lys Leu Lys Pro Thr His Ala Glu Arg Thr Val Phe Gly Glu Gly
    130                 135                 140 gac ggc agc cat ctc gcg gtg cac gat acc gcc atc ggg cgc ctc ggc        480
Asp Gly Ser His Leu Ala Val His Asp Thr Ala Ile Gly Arg Leu Gly
145                 150                 155                 160 gcg ctc tgt tgc tgg gag cac atc cag cca ttg tcg aaa tac gcc atg        528
Ala Leu Cys Cys Trp Glu His Ile Gln Pro Leu Ser Lys Tyr Ala Met
                165                 170                 175 tac gcc gcc gac gaa cag gtc cac gtc gcg tcg tgg ccg agc ttc agc        576
Tyr Ala Ala Asp Glu Gln Val His Val Ala Ser Trp Pro Ser Phe Ser
            180                 185                 190 ctc tat cgc ggc atg gcc tat gcg ctc gga ccg gag gtc aat acc gcc        624
Leu Tyr Arg Gly Met Ala Tyr Ala Leu Gly Pro Glu Val Asn Thr Ala
        195                 200                 205 gca agc cag atc tac gcg gtc gag ggc ggc tgc tac gtg ctg gcg tcg        672
Ala Ser Gln Ile Tyr Ala Val Glu Gly Gly Cys Tyr Val Leu Ala Ser
    210                 215                 220 tgc gcg acc gtt tcg ccg gag atg atc aag gta ttg gtg gat acg ccc        720
Cys Ala Thr Val Ser Pro Glu Met Ile Lys Val Leu Val Asp Thr Pro
225                 230                 235                 240 gac aag gag atg ttc ctc aag gcc ggc ggc ggt ttt gcc atg att ttc        768
Asp Lys Glu Met Phe Leu Lys Ala Gly Gly Gly Phe Ala Met Ile Phe
                245                 250                 255 ggg ccc gac ggc cgc gcc ctg gcc gag ccg ctc ccg gag acc gaa gag        816
Gly Pro Asp Gly Arg Ala Leu Ala Glu Pro Leu Pro Glu Thr Glu Glu
            260                 265                 270 gga ctg ctg gtc gcc gat atc gac ctc ggc atg atc gcg ttg gcc aag        864
Gly Leu Leu Val Ala Asp Ile Asp Leu Gly Met Ile Ala Leu Ala Lys
        275                 280                 285 gcg gcg gcc gat ccg gcg ggc cac tat tca cgg ccc gac gta acg cgg        912
Ala Ala Ala Asp Pro Ala Gly His Tyr Ser Arg Pro Asp Val Thr Arg
    290                 295                 300 ctg ctg ctg gat cga cgt ccg gcc caa cgc gtc gtc acg ctt gat gcc        960
Leu Leu Leu Asp Arg Arg Pro Ala Gln Arg Val Val Thr Leu Asp Ala
305                 310                 315                 320
```

```
gca ttc gaa ccg caa aac gag gac aag ggc gac gcg ccc gcg ctg cgc    1008
Ala Phe Glu Pro Gln Asn Glu Asp Lys Gly Asp Ala Pro Ala Leu Arg
            325                 330                 335 gtg gtg gcg gaa agc gcc gcc gcc gcg cag tag                        1041
Val Val Ala Glu Ser Ala Ala Ala Ala Gln
340                 345
```

<210> SEQ ID NO 2
<211> LENGTH: 346
<212> TYPE: PRT
<213> ORGANISM: Unknown
<220> FEATURE:
<223> OTHER INFORMATION: Description of Unknown Organism: Obtained from an environmental sample

<400> SEQUENCE: 2

```
Met Ser Glu Pro Met Thr Lys Tyr Arg Gly Ala Ala Val Gln Ala Ala
 1               5                  10                  15

Pro Val Phe Leu Asp Leu Asp Arg Thr Val Glu Lys Ala Ile Gly Leu
                20                  25                  30

Ile Glu Gln Ala Ala Lys Gln Asp Val Arg Leu Ile Ala Phe Pro Glu
            35                  40                  45

Thr Trp Ile Pro Gly Tyr Pro Phe Trp Ile Trp Leu Gly Ala Pro Ala
        50                  55                  60

Trp Gly Met Arg Phe Val Gln Arg Tyr Phe Glu Asn Ser Leu Val Arg
65                  70                  75                  80

Gly Ser Lys Gln Trp Gln Ala Leu Ala Asp Ala Ala Arg Arg His Gly
                85                  90                  95

Met His Val Val Ala Gly Tyr Ser Glu Arg Ala Gly Gly Ser Leu Tyr
            100                 105                 110

Met Gly Gln Ala Ile Phe Gly Pro Asp Gly Asp Leu Ile Ala Ala Arg
        115                 120                 125

Arg Lys Leu Lys Pro Thr His Ala Glu Arg Thr Val Phe Gly Glu Gly
130                 135                 140

Asp Gly Ser His Leu Ala Val His Asp Thr Ala Ile Gly Arg Leu Gly
145                 150                 155                 160

Ala Leu Cys Cys Trp Glu His Ile Gln Pro Leu Ser Lys Tyr Ala Met
                165                 170                 175

Tyr Ala Ala Asp Glu Gln Val His Val Ala Ser Trp Pro Ser Phe Ser
            180                 185                 190

Leu Tyr Arg Gly Met Ala Tyr Ala Leu Gly Pro Glu Val Asn Thr Ala
        195                 200                 205

Ala Ser Gln Ile Tyr Ala Val Glu Gly Gly Cys Tyr Val Leu Ala Ser
    210                 215                 220

Cys Ala Thr Val Ser Pro Glu Met Ile Lys Val Leu Val Asp Thr Pro
225                 230                 235                 240

Asp Lys Glu Met Phe Leu Lys Ala Gly Gly Phe Ala Met Ile Phe
                245                 250                 255

Gly Pro Asp Gly Arg Ala Leu Ala Glu Pro Leu Pro Glu Thr Glu Glu
            260                 265                 270

Gly Leu Leu Val Ala Asp Ile Asp Leu Gly Met Ile Ala Leu Ala Lys
        275                 280                 285

Ala Ala Ala Asp Pro Ala Gly His Tyr Ser Arg Pro Asp Val Thr Arg
    290                 295                 300

Leu Leu Leu Asp Arg Arg Pro Ala Gln Arg Val Val Thr Leu Asp Ala
305                 310                 315                 320

Ala Phe Glu Pro Gln Asn Glu Asp Lys Gly Asp Ala Pro Ala Leu Arg
```

```
                        325                 330                 335
        Val Val Ala Glu Ser Ala Ala Ala Gln
                    340                 345

<210> SEQ ID NO 3
<211> LENGTH: 1014
<212> TYPE: DNA
<213> ORGANISM: Unknown
<220> FEATURE:
<223> OTHER INFORMATION: Description of Unknown Organism: Obtained from
      an environmental sample
<220> FEATURE:
<221> NAME/KEY: CDS
<222> LOCATION: (1)..(1014)

<400> SEQUENCE: 3 atg aaa gaa gct atc aag gtc gcc tgc gtg caa gcc gcc ccg atc tac      48
Met Lys Glu Ala Ile Lys Val Ala Cys Val Gln Ala Ala Pro Ile Tyr
 1               5                  10                  15 atg gat ttg gag gcg acg gtg gac aaa acc att gag ttg atg gaa gaa      96
Met Asp Leu Glu Ala Thr Val Asp Lys Thr Ile Glu Leu Met Glu Glu
             20                  25                  30 gca gca cgt aat aat gct cgt ctg atc gcc ttt ccg gaa act tgg att     144
Ala Ala Arg Asn Asn Ala Arg Leu Ile Ala Phe Pro Glu Thr Trp Ile
         35                  40                  45 cca ggc tac cca tgg ttt ctt tgg ctt gac tca cca gca tgg gca atg     192
Pro Gly Tyr Pro Trp Phe Leu Trp Leu Asp Ser Pro Ala Trp Ala Met
     50                  55                  60 caa ttt gta cgc caa tac cat gag aac tca ttg gag ttg gat ggc cct     240
Gln Phe Val Arg Gln Tyr His Glu Asn Ser Leu Glu Leu Asp Gly Pro
 65                  70                  75                  80 caa gct aag cgc att tca gat gca gcc aag cgg ttg gga atc atg gtc     288
Gln Ala Lys Arg Ile Ser Asp Ala Ala Lys Arg Leu Gly Ile Met Val
                 85                  90                  95 acc ctg ggg atg agt gaa cgg gtc ggt ggc acc ctt tac atc agt cag     336
Thr Leu Gly Met Ser Glu Arg Val Gly Gly Thr Leu Tyr Ile Ser Gln
            100                 105                 110 tgg ttc ata ggc gat aat ggt gac acc att ggg gcc cgg cga aag ttg     384
Trp Phe Ile Gly Asp Asn Gly Asp Thr Ile Gly Ala Arg Arg Lys Leu
        115                 120                 125 aaa cct act ttt gtt gaa cgt act ttg ttc ggc gaa ggg gat ggt tca     432
Lys Pro Thr Phe Val Glu Arg Thr Leu Phe Gly Glu Gly Asp Gly Ser
    130                 135                 140 tcg cta gcg gtt ttc gag acg tct gtt gga agg ctg ggt ggc tta tgc     480
Ser Leu Ala Val Phe Glu Thr Ser Val Gly Arg Leu Gly Gly Leu Cys
145                 150                 155                 160 tgt tgg gag cac ctt caa ccg cta aca aaa tac gct ttg tat gca caa     528
Cys Trp Glu His Leu Gln Pro Leu Thr Lys Tyr Ala Leu Tyr Ala Gln
                165                 170                 175 aat gaa gag att cat tgt gcg gct tgg ccg agc ttt agc ctt tat cct     576
Asn Glu Glu Ile His Cys Ala Ala Trp Pro Ser Phe Ser Leu Tyr Pro
            180                 185                 190 aat gcg gcg aaa gcc ctg ggg cct gat gtc aat gta gcg gcc tct cga     624
Asn Ala Ala Lys Ala Leu Gly Pro Asp Val Asn Val Ala Ala Ser Arg
        195                 200                 205 atc tat gcc gtt gaa ggg caa tgc ttc gta cta gcg tcg tgt gcg ctc     672
Ile Tyr Ala Val Glu Gly Gln Cys Phe Val Leu Ala Ser Cys Ala Leu
    210                 215                 220 gtt tca caa tcc atg atc gat atg ctt tgt aca gat gac gaa aag cat     720
Val Ser Gln Ser Met Ile Asp Met Leu Cys Thr Asp Asp Glu Lys His
225                 230                 235                 240 gcg ttg ctt ctg gct ggt ggt gga cac tca cgt atc ata ggg cct gat     768
Ala Leu Leu Leu Ala Gly Gly Gly His Ser Arg Ile Ile Gly Pro Asp
```

```
            Ala Leu Leu Leu Ala Gly Gly His Ser Arg Ile Ile Gly Pro Asp
                            245                 250                 255 ggt ggt gac ttg gtc gcg cct ctt gcc gaa aat gaa gag ggt att ctc         816
Gly Gly Asp Leu Val Ala Pro Leu Ala Glu Asn Glu Glu Gly Ile Leu
            260                 265                 270 tac gca aac ctt gat cct gga gta cgc atc ctt gct aaa atg gcg gca         864
Tyr Ala Asn Leu Asp Pro Gly Val Arg Ile Leu Ala Lys Met Ala Ala
            275                 280                 285 gac cct gct ggt cat tat tcc cgt ccc gac att act cgc ttg cta ata         912
Asp Pro Ala Gly His Tyr Ser Arg Pro Asp Ile Thr Arg Leu Leu Ile
        290                 295                 300 gat cgc agc cct aaa tta ccg gta gtt gaa att gaa ggt gat ctt cgt         960
Asp Arg Ser Pro Lys Leu Pro Val Val Glu Ile Glu Gly Asp Leu Arg
305                 310                 315                 320 cct tac gct ttg ggt aaa gcg tct gag acg ggt gcg caa ctc gaa gaa        1008
Pro Tyr Ala Leu Gly Lys Ala Ser Glu Thr Gly Ala Gln Leu Glu Glu
                325                 330                 335 att tga                                                                1014
Ile

<210> SEQ ID NO 4
<211> LENGTH: 337
<212> TYPE: PRT
<213> ORGANISM: Unknown
<220> FEATURE:
<223> OTHER INFORMATION: Description of Unknown Organism: Obtained from
      an environmental sample

<400> SEQUENCE: 4

Met Lys Glu Ala Ile Lys Val Ala Cys Val Gln Ala Ala Pro Ile Tyr
  1               5                  10                  15

Met Asp Leu Glu Ala Thr Val Asp Lys Thr Ile Glu Leu Met Glu Glu
             20                  25                  30

Ala Ala Arg Asn Asn Ala Arg Leu Ile Ala Phe Pro Glu Thr Trp Ile
         35                  40                  45

Pro Gly Tyr Pro Trp Phe Leu Trp Leu Asp Ser Pro Ala Trp Ala Met
     50                  55                  60

Gln Phe Val Arg Gln Tyr His Glu Asn Ser Leu Glu Leu Asp Gly Pro
 65                  70                  75                  80

Gln Ala Lys Arg Ile Ser Asp Ala Ala Lys Arg Leu Gly Ile Met Val
                 85                  90                  95

Thr Leu Gly Met Ser Glu Arg Val Gly Gly Thr Leu Tyr Ile Ser Gln
            100                 105                 110

Trp Phe Ile Gly Asp Asn Gly Asp Thr Ile Gly Ala Arg Arg Lys Leu
        115                 120                 125

Lys Pro Thr Phe Val Glu Arg Thr Leu Phe Gly Glu Gly Asp Gly Ser
    130                 135                 140

Ser Leu Ala Val Phe Glu Thr Ser Val Gly Arg Leu Gly Gly Leu Cys
145                 150                 155                 160

Cys Trp Glu His Leu Gln Pro Leu Thr Lys Tyr Ala Leu Tyr Ala Gln
                165                 170                 175

Asn Glu Glu Ile His Cys Ala Ala Trp Pro Ser Phe Ser Leu Tyr Pro
            180                 185                 190

Asn Ala Ala Lys Ala Leu Gly Pro Asp Val Asn Val Ala Ala Ser Arg
        195                 200                 205

Ile Tyr Ala Val Glu Gly Gln Cys Phe Val Leu Ala Ser Cys Ala Leu
    210                 215                 220

Val Ser Gln Ser Met Ile Asp Met Leu Cys Thr Asp Asp Glu Lys His
```

-continued

```
225                 230                 235                 240
Ala Leu Leu Leu Ala Gly Gly Gly His Ser Arg Ile Ile Gly Pro Asp
                245                 250                 255

Gly Gly Asp Leu Val Ala Pro Leu Ala Glu Asn Glu Glu Gly Ile Leu
            260                 265                 270

Tyr Ala Asn Leu Asp Pro Gly Val Arg Ile Leu Ala Lys Met Ala Ala
        275                 280                 285

Asp Pro Ala Gly His Tyr Ser Arg Pro Asp Ile Thr Arg Leu Leu Ile
    290                 295                 300

Asp Arg Ser Pro Lys Leu Pro Val Val Glu Ile Glu Gly Asp Leu Arg
305                 310                 315                 320

Pro Tyr Ala Leu Gly Lys Ala Ser Glu Thr Gly Ala Gln Leu Glu Glu
                325                 330                 335

Ile
```